United States Patent [19]

Plassche, Jr.

[11] Patent Number: 5,300,045
[45] Date of Patent: Apr. 5, 1994

[54] INTERVENTIONAL NEEDLE HAVING AN AUTOMATICALLY CAPPING STYLET

[76] Inventor: Walter M. Plassche, Jr., 1209 Clover St., Rochester, N.Y. 14610

[21] Appl. No.: 48,403

[22] Filed: Apr. 14, 1993

[51] Int. Cl.5 .............................................. A61M 5/00
[52] U.S. Cl. .................................... 604/263; 604/158; 604/160; 604/161; 604/162; 604/164; 604/166; 604/192; 604/198; 604/239; 604/264
[58] Field of Search .............. 604/110, 117, 158, 160, 604/161, 162, 163, 164, 165, 166, 167, 170, 192, 198, 239, 263, 264; 606/185

[56] References Cited

U.S. PATENT DOCUMENTS

| | | |
|---|---|---|
| 4,804,371 | 2/1989 | Vaillancourt ...................... 604/263 |
| 4,900,311 | 2/1990 | Stern . |
| 4,929,241 | 5/1990 | Kulli . |
| 4,932,940 | 6/1990 | Walker . |
| 5,026,356 | 6/1991 | Smith . |
| 5,049,136 | 9/1991 | Johnson ........................... 604/198 |
| 5,059,180 | 10/1991 | McLees ............................. 604/110 |
| 5,098,401 | 3/1992 | DeLange . |
| 5,104,384 | 4/1992 | Perry . |
| 5,108,379 | 4/1992 | Dolgin . |
| 5,135,504 | 8/1992 | McLees ............................. 604/164 |
| 5,147,327 | 9/1992 | Johnson ........................... 604/198 |
| 5,176,656 | 1/1993 | Bayless . |
| 5,183,468 | 2/1993 | McLees ............................. 604/110 |

FOREIGN PATENT DOCUMENTS 3802353 1/1988 Fed. Rep. of Germany ...... 604/192

Primary Examiner—C. Fred Rosenbaum
Assistant Examiner—Noelle Kent Gring
Attorney, Agent, or Firm—Martin Lukacher

[57] ABSTRACT

The tip of a stylet which is received in a needle cannula is automatically capped in a guard body when the stylet is withdrawn from the cannula. The stylet may be reassembled in the cannula and put into working position, with the point of the tip extending from the cannula shaft, by reinserting the stylet and guard into the cannula hub. The guard contains an arm which moves into blocking position with respect to the tip of the stylet when it is withdrawn from the cannula by following a cam surface on the cannula hub (either inside or outside the hub for different styles of needle cannulas). The arm may be spring biased, across a hole in the guard in which the stylet is slidably disposed into interfering relationship with the arm. The cam surface urges the arm to bring a portion thereof which protects the point of the tip of the stylet and captures it inside the guard. The arm and cam prevent removal of the stylet from the cannula until the tip is covered and protected by the guard, thereby automatically capping the tip of the stylet to prevent potentially dangerous, inadvertent, or accidental sticking of medical personnel. The interventional needle apparatus may be used as an angiographic needle and for other purposes, wherever access to vessels, kidneys or other body parts as for the insertion of catheters, infusions or drainage of body fluids including spinal fluid is required or where tissue is obtained by needle biopsy.

18 Claims, 8 Drawing Sheets

INTERVENTIONAL NEEDLE HAVING AN AUTOMATICALLY CAPPING STYLET

DESCRIPTION

The present invention relates to instruments for accessing subcutaneous tissue regions and vessels in the course of surgical procedures such as angiography, biopsy, infusion, puncturing (as of a kidney with an obstructed drainage system for insertion of a drainage catheter and particularly to interventional needle apparatus provided by an assembly of a needle cannula and a stylet in which the point or penetrating tip of the stylet is automatically capped when withdrawn from the cannula.

The invention is especially suitable for providing an angiographic needle assembly of a cannula and stylet for use by an angiographer in providing access to a vessel (e.g. an artery or vein), for insertion of a catheter. Features of the invention will be found useful wherever it is desirable to cap a point of an instrument having a shaft so as to avoid inadvertent contact and pricking by medical personnel who make use thereof. The needle assembly will also have universal application in a wide range of interventional procedures.

Various caps and sleeves are provided with injection devices such as syringes and alike for capping the needles thereof to prevent accidental puncturing of the skin of personnel who come in contact therewith after use thereof. Even so called disposable injection devices must in certain instances be capped after use to prevent such accidental contact. A number of approaches for automatic capping or recapping have been suggested, however few have been generally accepted for use, principally because of difficulty in fabrication, cost or use thereof.

It is a feature of the present invention to provide an interventional needle apparatus of the type which utilizes a cannula in which the needle or stylet is located in order to automatically cap the tip and the penetrating point of the stylet, except when the stylet is in working position in the cannula.

It is a feature of the invention to utilize a guard and a cannula which have elements or portions thereof which are engageable with each other when the guard enters the hub of the cannula so as to articulate an arm movably mounted in the guard between positions where the arm is in interfering relationship with the movement of the stylet except when the stylet is guarded in the cannula itself or is in working position with the point extending out of the end of the cannula.

It is a feature of the invention, not only to protect or guard the point of the stylet after it is withdrawn, but also to lock the stylet in the cannula against being withdrawn until the penetrating point is protected within the guard body.

It is a further feature of the invention to provide an instrument having a penetrating stylet (which term is intended to include stylets, needles and other devices having a tip for accessing a body region, such as a vessel, organ, tumor or other internal body part) which guards against accidental or inadvertent puncturing so as to enable the instrument to be used a number of times in the course of a medical procedure or when the device is to be disposed of, (thrown away) thereby guarding against the possibility of unintentional pricking, scratching or cutting by the point of the penetrating device.

It is a still further feature of the invention to provide interventional needle apparatus of the type for accessing an internal anatomical part or region having a penetrating stylet which is protected when the stylet is withdrawn from a cannula in which it is disposed, prior to and in the course of the accessing procedure, which apparatus may be used in the way it is normally and conventionally used, without special steps in the procedure to accommodate or to operate the protective component thereof.

Briefly described, the invention provides interventional needle apparatus for accessing an internal anatomical region or part. The apparatus has a cannula with a tubular shaft and a hub. The hub has an opening leading to the shaft section of the cannula, preferably in the case of an angiographic cannula, via a funnel for leading a guide wire into a vessel which is accessed. The apparatus also has a stylet with a shaft and a penetrating tip or point. When in working position, prior to accessing the anatomical region is disposed inside the tubular shaft of the cannula with the point of the tip extending out of the tubular shaft. The stylet is withdrawn from the cannula in the course of the procedure for accessing the internal anatomical region. The invention provides a guard for capping the tip when the stylet is withdrawn in the course of the procedure. The stylet is withdrawn in angiographic and other procedures involving the insertion of the guide wire, or when another device such as a syringe is attached to the cannula hub, for infusion of fluid into the anatomical region being accessed and for other purposes. The stylet is an assembly with a guard body having a hole which is slidably disposed on the stylet shaft, with the shaft extending through the hole. The guard body has a first surface thereof (e.g. a step between longitudinally spaced parts of the hole of larger and smaller diameters). This surface is spaced inwardly of the guard body a distance sufficient to locate the tip within the guard body when a surface of the stylet (e.g. a shoulder spaced from the point of the tip) is in contact so as to locate the tip within the guard body. The guard body is receivable at least in part in the opening in the hub. The hub and guard body have surfaces which are engageable with each other and limit the extent to which the guard body is disposed in the hub opening when received (inserted) therein. A slot in the guard body crosses the hole in the guard body in which the stylet shaft is slidably disposed. An arm is located in the slot and has a portion moveable from a first position, in interfering relationship with the movement of the stylet with respect to the cannula, and a second position out of interfering relationship with the movement of the stylet. The hub of the cannula has a cam surface engageable with the arm when the guard body enters the hub opening to be received, at least in part, therein, and also when the guard body leaves (is withdrawn from) the hub opening. The movement of the arm with respect to the cam surface moves the arm between these positions, thereby automatically capping the stylet tip when the stylet is withdrawn from the cannula.

The foregoing and other objects, features, and advantages of the invention, as well as presently preferred embodiments thereof, will become more apparent from a reading of the following description in connection with the accompanying drawings in which.

Figure 8:
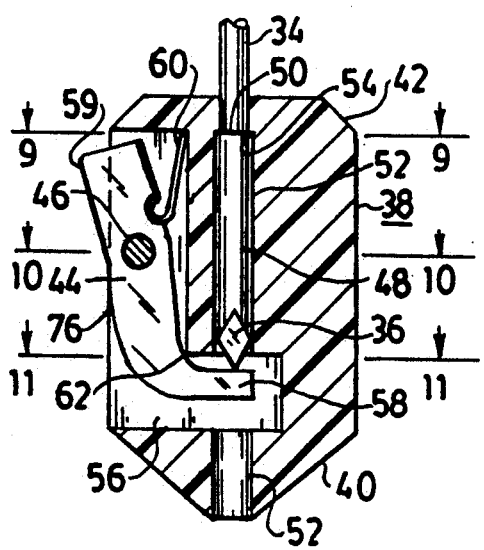
FIG. 8 is an enlarged, sectional view of the guard body in the position thereof shown in FIG. 7, the view being taken along the line 8—8 in FIGS. 9, 10 and 11.
Figure 12:
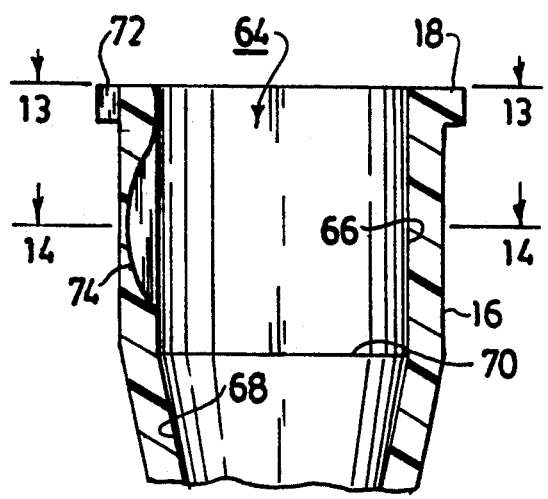
Figure 9:
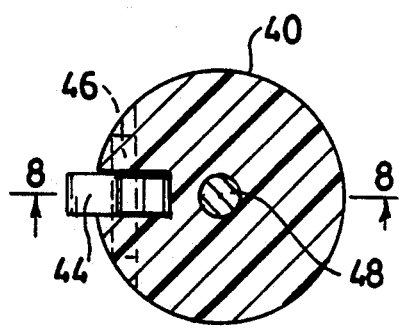
Figure 13:
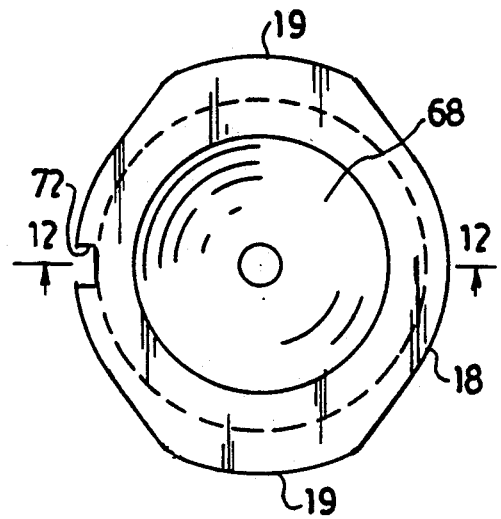
Figure 10:
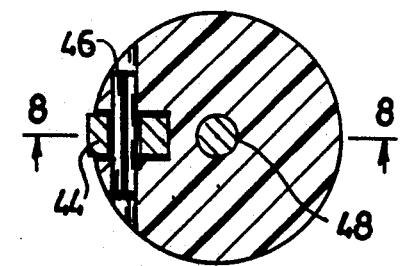
Figure 11:
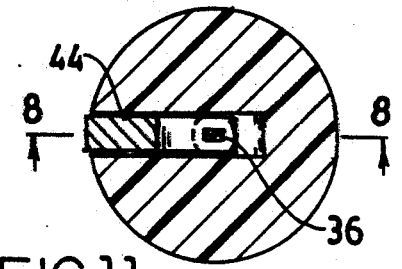
Figure 14:
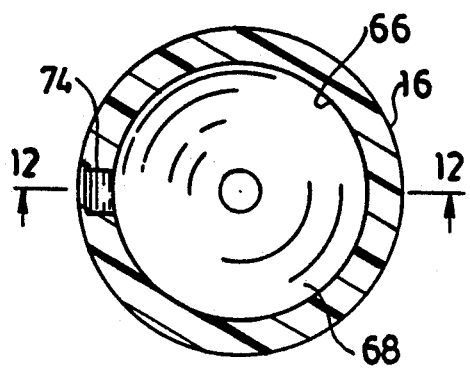
Figure 15:
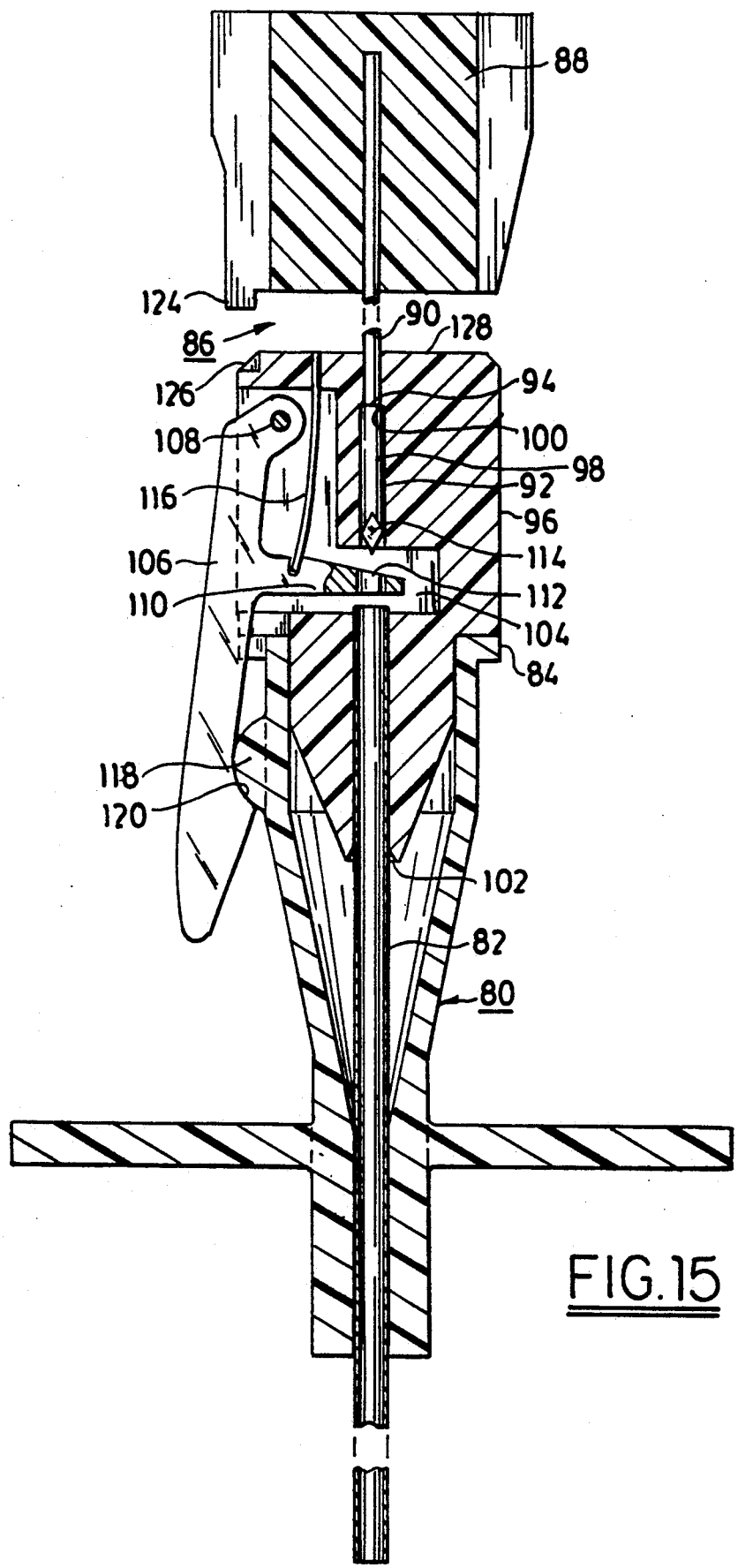
Figure 16:
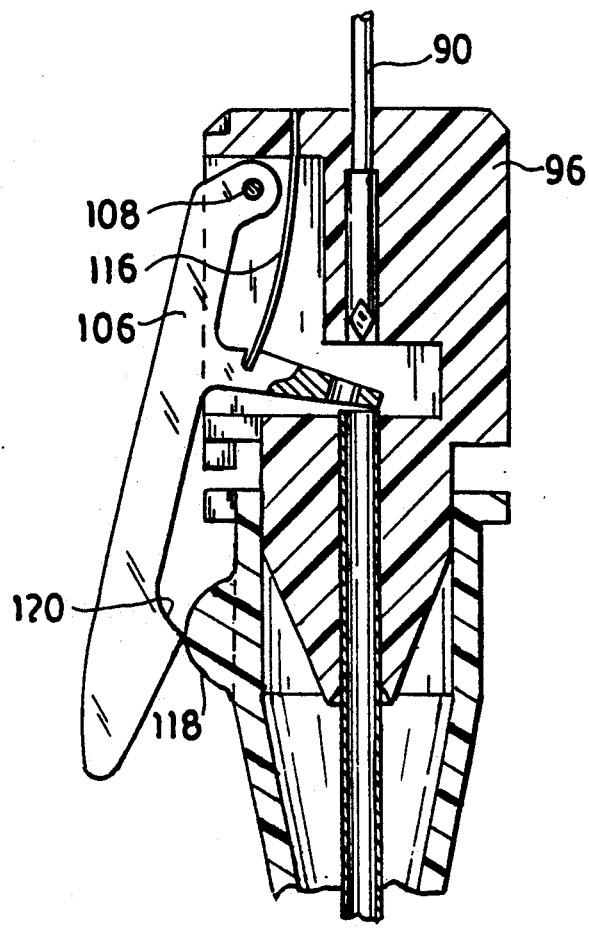
Figure 17:
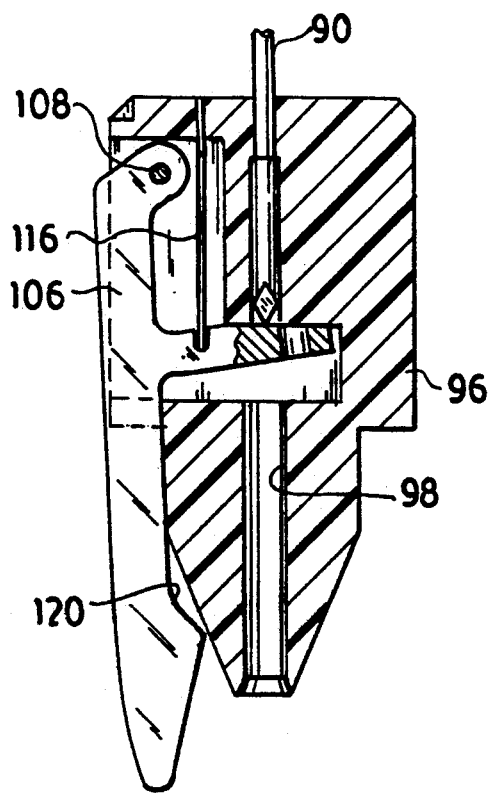

FIGS. 9, 10 and 11 are sectional views through successively lower vertical planes perpendicular to the longitudinal axis of the hole in which the stylet is disposed in the guard body, the views being taken along the lines 9—9, 10—10 and 11—11 in FIG. 8;

FIG. 12 is a fragmentary, sectional view of the hub of the cannula of the instrument shown in FIGS. 1-7, the views being taken along the line 12—12 in FIGS. 13 and 14;

FIGS. 13 and 14 are respectively an end view and a sectional view taken along a line perpendicular to the longitudinal axis of the cannula, the views being taken along the lines 13—13 and 14—14 in FIG. 12;

FIG. 15 is a sectional view of an interventional needle apparatus utilizing a cannula of the type where the tubular shaft thereof extends slightly above the rim of the hub of the cannula and where the guard body of the stylet assembly is modified for use with such a cannula, in accordance with another embodiment of the invention, the view showing the position of the stylet and cannula during their assembly, or just prior to being separated from the cannula upon withdrawal;

FIG. 16 is a view similar to FIG. 15, but with the guard further out of the cannula from its position in FIG. 15 and as the stylet is being withdrawn; and FIG. 17 is a view of the tip region of the stylet and the guard body, which like FIGS. 15 and 16 are sectional views along a longitudinal plane through the axis of instrument, but after the stylet has already been withdrawn, showing the arm of the guard body in position capturing and protecting the tip portion of the stylet within the guard body.

Figure 1:
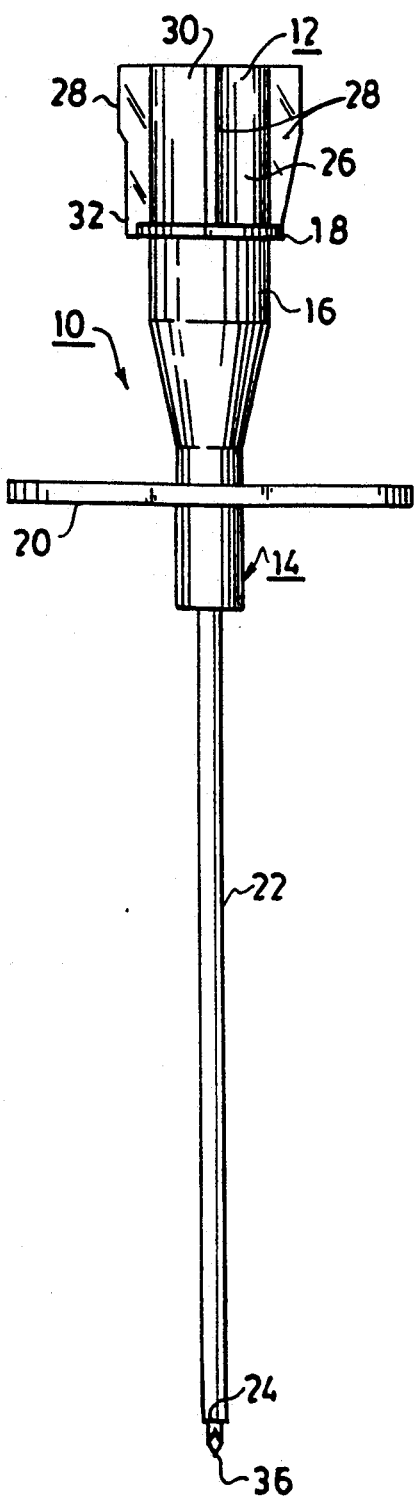
FIG. 1 is an elevational view of an interventional needle apparatus (a cannula and stylet assembly especially suitable for angiography) shown in working position.
Figure 2:
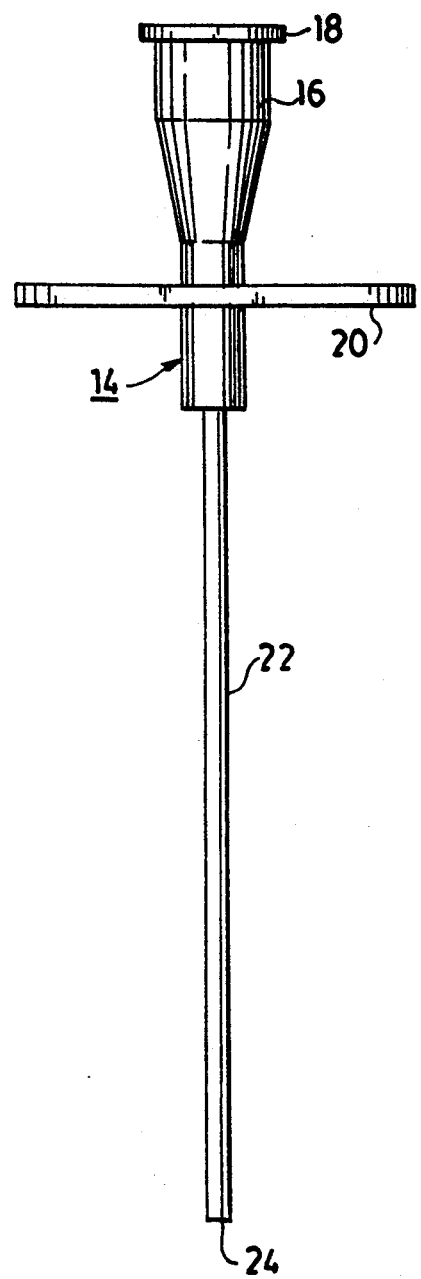
FIG. 2 is an elevational view of the cannula alone.
Figure 3:
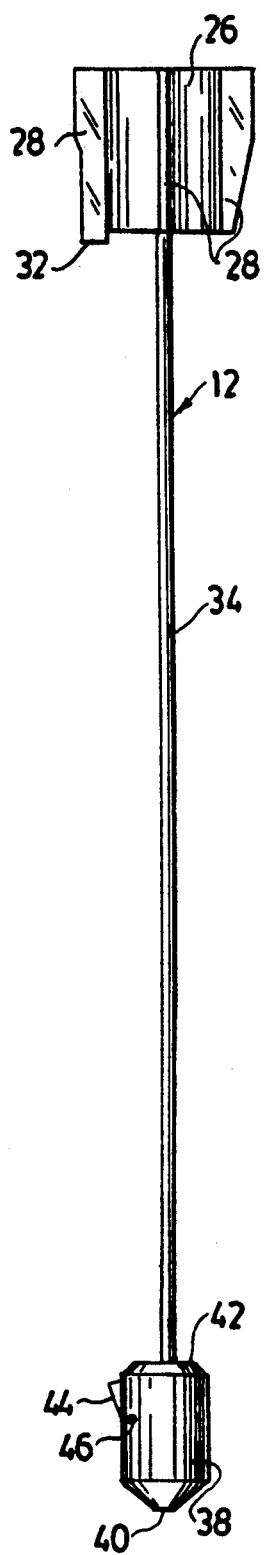
FIG. 3 is an elevational view of the stylet alone.

Referring to FIGS. 1, 2 and 3 there is shown interventional needle apparatus 10 provided an assembly of a stylet 12 and a cannula (sometimes called a needle cannula) 14. The cannula 14 has a hub 16 with a lip or rim 18 at the entrance end thereof. A flange 20, which is an oblong plate, is integral with the hub 16. The cannula also has a tubular shaft 22 extending away from the hub to an exit end 24. Preferably the shaft 22 is of metal (stainless steel) while the rest of the cannula 14 is made of plastic. The stylet 12 has a handle 26 with ribs 28 extending from a cylindrical core 30. One of the ribs extends below the core 30 and defines a key 32. The stylet has a shaft, or inner stylet section, 34 with a penetrating point or tip 36. A guard body 38 is slidably mounted on the stylet shaft 34. The guard body has a cylindrical outer periphery and tapered or frusto conical opposite ends 40 and 42. An arm 44 is mounted in the guard for movement into and out of interfering relationship with the stylet shaft and serves to block the tip from movement out of the guard body 38 as well as to lock the guard body 38 in the cannula, except when it is withdrawn with the tip 36 protected and enclosed in the guard body 38. The stylet shaft 34, and a pin 46 which pivotally mounts the arm 44 in the guard body 38, are preferably of metal (stainless steel). The rest of the stylet 12 may be made of plastic. A suitable plastic for the plastic parts of the instrument is polycarbonate.

The instrument as shown in FIG. 1 does not appear different from a conventional interventional needle of the type which is commercially available. The conventional interventional needle does not have a guard arranged on the stylet nor does it have a hub which cooperates with the guard in accordance with the features of this invention. The interventional needle as shown in FIG. 1, like the conventional device of this type, may be supplied with a sleeve or cover extending around the cannula shaft 22 and over the tip 36. This sleeve is removed prior to use of the interventional needle in obtaining access to a vessel or other region of the anatomy.

FIGS. 8 to 10 show the stylet shaft 34 and the guard 38 when in the position thereof shown in FIG. 3, i.e., withdrawn from the cannula. The stylet is withdrawn from the cannula after the instrument provides access to the desired anatomical region, and when withdrawn may be reassembled with the cannula for repeated use. For example, in angiography it is desirable to use the instrument to penetrate a vessel first through the groin region of one leg and then through the groin region of the other leg. Also in some cases several attempts must be made to access a vessel. Then it is desirable to use the same instrument on each attempt. The invention enables the same instrument to be used without exposing the medical personnel to accidental contact with the needle because, after the stylet is withdrawn, the tip is captured and guarded within the guard body 38.

The stylet shaft 34 is provided with a tip portion 48 which ends at the point 36 and has a diameter larger than the remainder of the shaft 34 thereby defining a surface at a shoulder 50. The point 36 is shown as a diamond shape point; however it may be a chisel or beveled point. In such instances the key 32 denotes the location of the chisel or bevel surface. The key serves a dual purpose in this invention of indicating the angular position with respect to the axis of the shaft 34 of the arm 44. Alignment marks on the guard may also be used for this purpose.

An axial or longitudinal opening 52 in the guard body 38 has sections of larger and smaller diameter which defines a surface at a step 54. The step and shoulder are spaced a sufficient distance from the exit end of the guard through which the point 36 leaves the guard, as well as to where the arm 44 engages the point 36, so as to assure that the point 36 and the tip section 48 are within the guard 38 and captured therein by the arm 44 when the stylet 12 is withdrawn from the cannula 14.

The guard body 38 has a lateral or radially extending L-shaped slot 56 across which the pin 46 extends and pivotally mounts the arm 44 as a rocker arm or lever with portions on opposite sides of the pivot axis defined by the pin 46. One of these portions has a projection 58 in the form of an extension from the lower end thereof which is biased in blocking relationship with the opening 52 by a hair pin spring 60. Then the projection 58 is in interfering relationship with the stylet 34. In that position the arm is stopped at an edge 62 of the slot 56. When so stopped the opposite end portion 59 (above the pivot pin 46 and opposite to the spring 60) extends out of the slot 56 and is exposed from the guard along the outer, cylindrical periphery thereof. This exposed portion 59 engages the arm when the guard body is disposed in the cannula and causes the projection 58 to move out of interfering, blocking relationship with the stylet point 36, and also serves to lock the guard in the cannula until the stylet is withdrawn with its tip section 48 guarded, protected and captured in the guard body 38, which is the position shown in FIG. 8.

Referring to FIGS. 12–14, the hub of the cannula has an opening 64 with a cylindrical section 66, extending from the entrance and of the cannula at the rim 18, to an inwardly tapered or funnel section 68. The cylindrical section 66 and the funnel section 68 meet at a junction 70 where the funnel section narrows so that it stops and seats the guard body within the opening 64. The tapered end 40 assists in locating the guard body in the opening 64. The rim 18 has a notch 72 which receives the key 32 in the handle 26.

A depression or slot 74 extends outwardly from the inner periphery of the cylindrical section 66 of the opening 64 and defines a cam surface within the hub 16, and spaced from the entrance end thereof. A cam follower surface 76 of the arm 44 engages the cam surface defined by the depression or slot 74. The slot 74 is preferably aligned with the notch 72 so as to facilitate assembly of the stylet 12 and cannula 14. If desired, the depression may be annular and extend 360 degrees or less around the circumference of the cannula hub 16 thereby facilitating the location of the arm cam follower surface 76 in the slot or depression on assembly of the stylet with the cannula 14.

The engageable cam surfaces 74 and 76 provide a dual function; first they prevent insertion of the stylet into the cannula unless the stylet is properly aligned with the cannula, thus taking into account the angle of the bevel on certain types of stylet points, and second they enable the arm and hub to interlock, locking the guard inside the cannula except when the stylet tip section 48 is withdrawn so that the shoulder 50 is in engagement with the step 54. This assures that the tip is within the guard. There may be some cases where bodily fluids, for example bile, increase the friction between the stylet shaft 34 and the hole 52. The forces transferred to the guard upon withdrawal of the stylet then tend to allow the guard to be withdrawn from the cannula. Under such circumstances, the projection 58 will contact the side of the stylet shaft 34; this will prevent the arm portion, containing the cam surface 76, from leaving the slot 74. The guard then remains locked in the cannula and cannot be removed until the stylet is fully withdrawn so that its tip section 48 and particularly point 36 are captured and protected within the guard body 38.

Figure 4:
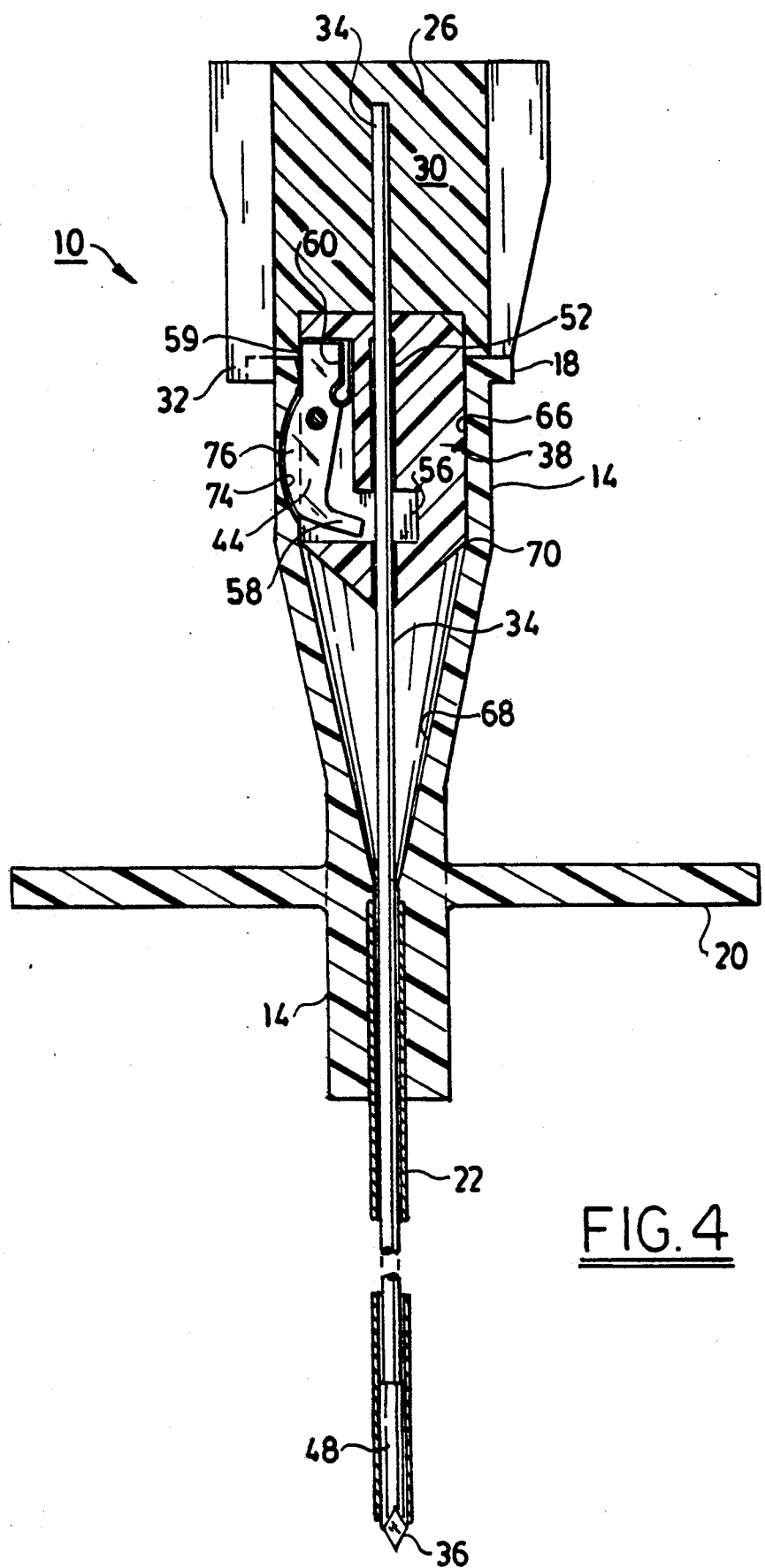
FIG. 4 is a sectional, elevational view, the section being taken along a plane through the longitudinal axis of the cannula and stylet of the instrument shown in FIG. 1 when in its working position.

FIG. 4 shows the instrument 10 in working position with the handle 26 seated on the rim 18 of the cannula and the arm out of interfering relationship with the stylet shaft 34 but in position locking the guard body 38 in the cannula hub 14.

Figure 5:
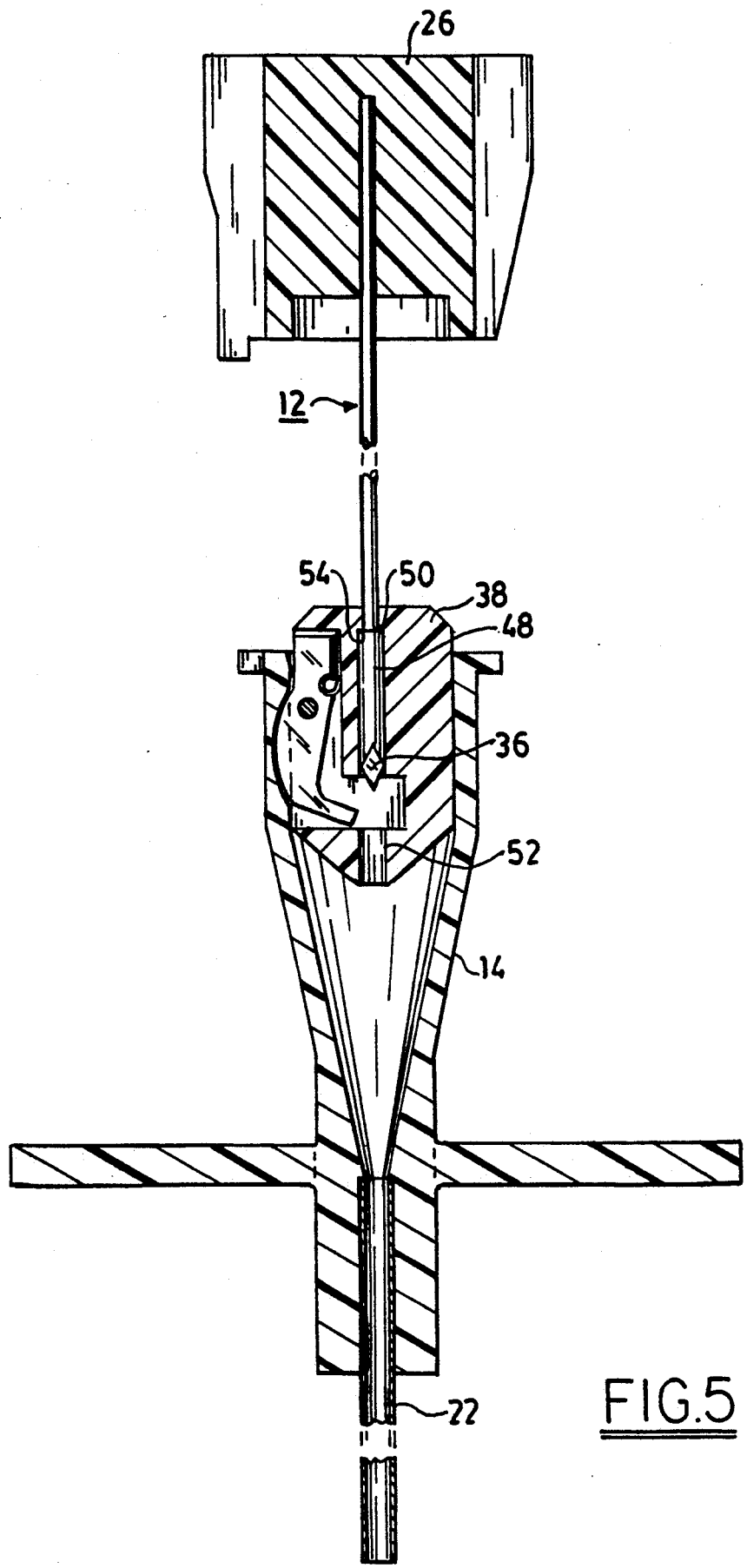
FIG. 5 is a view similar to FIG. 4 showing the stylet in the process of being withdrawn, but with the guard body thereof still within the cannula.
Figure 6:
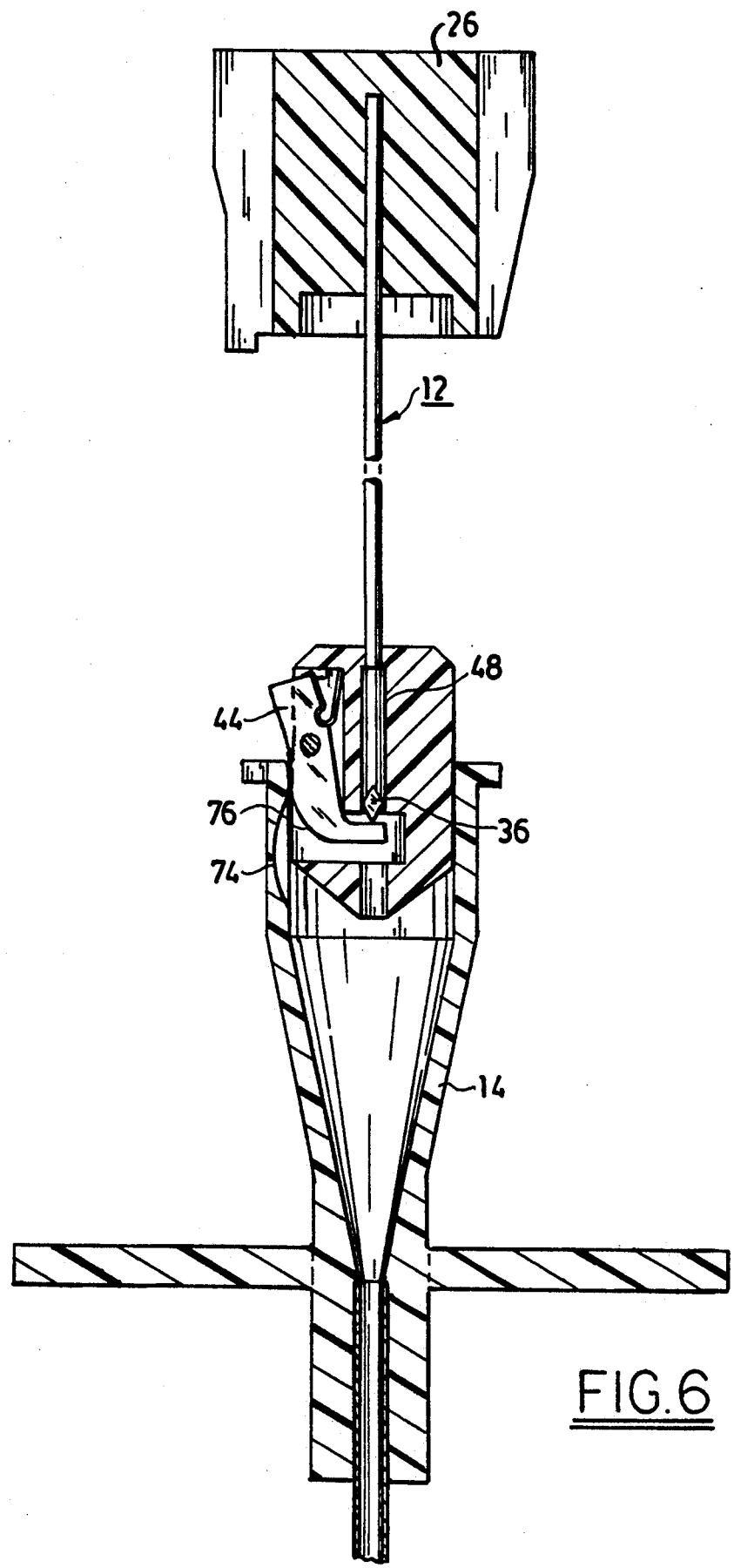
FIG. 6 is a view similar to FIG. 5 also showing the stylet in process of being withdrawn but with the guard body approximately halfway out of the cannula.
Figure 7:
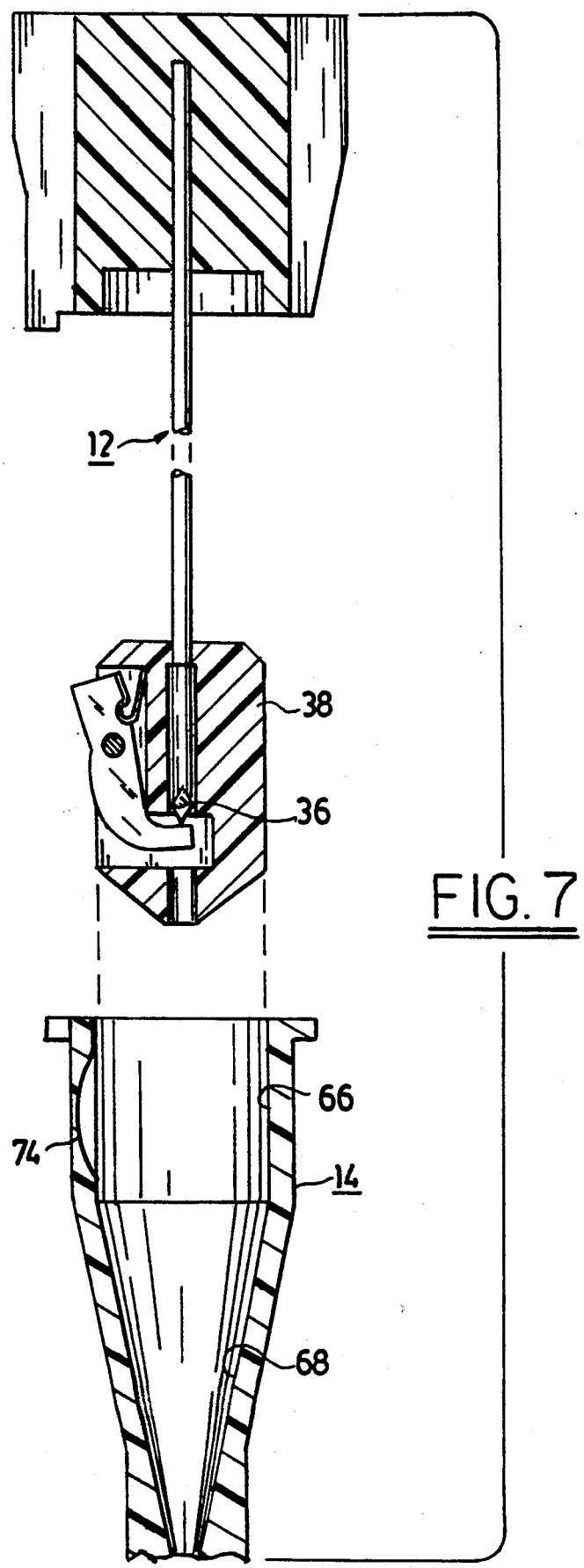
FIG. 7 is a view similar to FIG. 6 but showing the stylet completely withdrawn from the cannula.

In FIG. 5 the guard body is ready to be withdrawn because the shoulder 50 and step 54 are in engagement. Then the arm can be cammed out of the slot 74 as shown in FIG. 6. When completely removed, as shown in FIG. 7 the stylet 12 has the guard body 38 in the same position as shown in FIG. 3. On reinsertion it may be desirable to hold the guard body 38 and seat it in the cannula before pressing downwardly on the handle to extend the stylet shaft and tip to the working position as shown in FIG. 1. With the stylet withdrawn, a guide wire may be introduced into the cannula. The cam slot 74 is located near the top of the cannula hub in the cylindrical section 66 and does not interfere with the guidance of the guide wire by the funnel section 68 of the cannula 14. With the guide wire inserted, the cannula 14 may be removed and a catheter inserted around the guide wire in accordance with conventional procedures.

Referring to FIG. 15, there is shown a cannula 80 of the type having its tubular shaft 82 extending above the rim 84 at the entrance end thereof. This cannula is used with a stylet 86 having a handle 88 like the handle 26 and a stylet shaft 90 like the shaft 34 with a tip section 92 defining a shoulder 94. The stylet also has a guard body 96 with a longitudinal hole 98 along its axis which has a step 100 which engages the shoulder 94 for withdrawal of the guard body 96 from the hub of the cannula 80 as described in connection with FIGS. 1–14.

When seated on the rim 84, the guard 96 receives the tubular shaft 82 slidably within the end of the hole 98 near the exit end 102 of the guard 96. The shaft 82 extends into an L-shaped slot 104 in which an arm 106 is disposed.

The arm 106 is pivotally mounted on a pin 108 and has a projection 110 which extends across the hole 98. The hole 98 extends longitudinally through the guard body 96. The arm 106 has an aperture 112 which, when aligned as shown in FIG. 15, allows the stylet shaft 90 to extend therethrough and bring the stylet into working position in the tubular shaft 82 with the point 114 extending from the exit end of the shaft 82, much in the same way as the point 36 extends from the shaft 22 (see FIG. 1).

The arm 106 is biased by a spring 116 which may be a stainless steel strip. The spring 116 biases the projection 110 into interfering relationship with the movement of the stylet 90 across the hole 98 to the position shown in FIG. 17 when the guard body 96 is withdrawn from the hub 80 of the cannula.

In order to move the projection 110 and the arm 106 out of interfering relationship with the stylet 90 and to the position shown in FIG. 15, a protuberance 118 or cam lobe defines a cam surface on the outer periphery of the cylindrical part of the hub 80 which cooperates with a cam follower surface 120 on arm 106. Until the stylet 90 is fully withdrawn, so that the shoulder 94 and step 100 are in engagement, the cam surfaces 118 and 120 are in locking relationship and prevent the removal of the guard body 96 as shown in FIG. 15. Alignment of this stylet and the cam lobe 118 is facilitated by a key 124 in the handle 88 and a notch 126 on the exit end surface 128 of the guard body 96. The instrument shown in FIGS. 15–17 operates substantially in the same way as the instrument shown in FIGS. 1 to 14.

In both cases, and as shown in FIGS. 12 and 13, the rim 18 which may be of the same diameter around its entire circumference or made with lobes 19 cooperates with the thread of a coupling for connecting catheters, syringes or other devices to the cannula. This coupling is known in the art as a Luer lock and has a nipple which goes into sealing engagement with the inside of the cannula hub. Thus, the guarded instrument provided by the invention may be used much in the same way as a conventional interventional needle assembly in surgical procedures which require infusions or connections to drainage bags, solution bags or syringes as may be required in the procedures.

From the foregoing description it will be apparent that there has been provided interventional needle apparatus which has been improved by means which prevent exposure of the penetrating stylet thereof. Variations and modifications of the herein illustrated apparatus, within the scope of the invention, will undoubtedly become apparent to those skilled in the art. For example, a cam lobe on the outer surface of the cannula hub may be used on some types of needle assemblies which have a tubular cannula shaft that ends at the apex of the funnel portion of the hub (as in FIGS. 4 to 6). Accordingly the foregoing description should be taken as illustrative and not in a limiting sense.

I claim:

1. An interventional needle apparatus for accessing an internal anatomical region and having a cannula with a tubular shaft and a hub having an opening leading to the shaft thereof and also having a stylet having a shaft and a penetrating tip which, when in working relationship, is disposed inside the tubular shaft and the opening of the hub of the cannula with the point of the tip extending from the tubular shaft and which said stylet is withdrawn from said cannula in the course of a procedure for accessing of said internal anatomical region, the improvement for capping said tip when said stylet is withdrawn which comprises a guard body having a hole, said guard body being slidably disposed on said stylet shaft with said stylet shaft extending through said hole, said guard body having a first surface within said hole engageable with a shoulder surface of said stylet shaft and spaced inwardly in said guard body by a distance sufficient to locate said tip within said guard body when said first and said shoulder surfaces are engaged with each other, said guard body being receivable at least in part in said hub opening, said hub having hub surface and said guard body having a second surface which are engageable with each other and limit the extent to which said guard body is disposed in said hub opening when received therein, a slot in said guard body crossing said hole in said guard body in which said stylet shaft is slidably disposed, an arm in said slot connected to said guard body and having a first portion moveable from a first position in interfering relationship with the movement of said stylet with respect to said cannula and a second position out of said interfering relationship, said hub of said cannula having a cam surface engageable with a cam follower surface on said arm when said guard body enters said hub opening to be received at least in part therein and when said guard body leaves said hub opening for moving said arm between said second and first positions, respectively, thereby automatically capping said stylet tip when said stylet is withdrawn from said cannula.

2. The apparatus as set forth in claim 1 wherein said penetrating tip is at the end of said stylet shaft and is the end of a tip section having an outside diameter larger than said shaft to define a shoulder surface, said first surface within said hole of said guard body being defined by a step in said hole thereof, said guard body having opposite ends at an entrance through which said tip enters and from which said tip projects outwardly from said hole therein, respectively, said end through which said tip projects being spaced from said step a distance at least equal to the distance between said shoulder and said tip so that said tip is disposed within said guard body when said shoulder and step are in engagement with each other.

3. The apparatus according to claim 1 wherein said first and second surfaces of said guard body are separated from each other along the length direction of said hole through said guard body.

4. The apparatus according to claim 1 wherein said hub of said cannular has an outside surface which defines the outer periphery thereof and an inside surface which defines the outer periphery thereof and an inside surface which defines said opening, said cam surface extending over a portion of said inside surface.

5. The apparatus according to claim 4 wherein said cam surface portion includes a concave depression in said inside surface.

6. The apparatus according to claim 5 wherein said depression is a slot extending longitudinally of said hub.

7. The apparatus according to claim 6 wherein said hub has a rim, a slot in said rim in alignment with said slot which provides said depression and which defines said cam surface portion.

8. The apparatus according to claim 1 wherein said hub of said cannular has an outer peripheral surface and said cam surface is a protuberance extending outwardly from said outer peripheral surface.

9. The apparatus according to claim 8 wherein said arm has a portion which follows said cam surface and is disposed in part outside said guard body, said hub has a rim with a surface which defines said hub surface, a notch in said rim alignment with said cam surface and said arm received in said notch.

10. The apparatus according to claim 8 wherein said arm has a projection extending inwardly across said hole in said guard body in which said stylet shaft is slidably disposed, said projection defining said portion of said arm which is moveable into and out of interfering relationship with the movement of said stylet, said projection having a hole which is disposed in alignment with the hole in said guard body when in said second position out of said interfering relationship.

11. The apparatus according to claim 8 wherein said stylet has a handle having a key projecting beyond a lower handle surface along the outside of said handle, said guard body having an end facing said lower handle surface, a notch in the end of said guard body in alignment with said arm for receiving said key.

12. The apparatus according to claim 5 wherein said hub has an entrance end into which said stylet enters, said opening in said hub having a funnel shaped section therein and a cylindrical section extending between said funnel section and said entrance end of said hub and joining said funnel section at a junction, said junction defining said hub surface where its diameter is less than the diameter of said guard.

13. The apparatus according to claim 5 wherein said arm has a side facing outwardly of said guard body with a portion engageable with said hub along a surface thereof which defines said opening at an entrance end of said hub into which said stylet and said guard body enter into said opening in said hub, said side of said arm having a second portion shaped convexly which engages said concave depression whereby to lock said guard body in said hub opening when received therein.

14. The apparatus according to claim 13 wherein said arm is pivotally mounted to said guard body at a pin extending across said slot, said arm being a lever with said first portion and second portion on opposite sides of said pin and a spring in said guard body bearing against said arm on the side thereof opposite to said first portion for biasing said first portion outwardly and said second portion inwardly of said guard body into said interfering relationship.

15. The apparatus according to claim 14 wherein said arm has a projection extending inwardly from a side of said arm opposite to said outwardly facing side and on the same side of said pin as said second portion, said projection providing said interfering relationship with the movement of said stylet.

16. The apparatus according to claim 8 wherein said arm is pivotally mounted on a pin extending across said slot in said guard body, and a spring in said guard body biasing said arm to pivot inwardly about said pin.

17. The apparatus according to claim 1 wherein said arm is pivotally mounted in said guard body, and a spring in said guard body for biasing said arm to pivot towards said first position to provide said interfering relationship.

18. The apparatus according to claim 7 wherein said stylet has a handle at an end thereof opposite to said tip section, said handle having a key extending toward said tip section, said key being received in said slot in said rim.

* * * * *